(12) United States Patent
Platon et al.

(10) Patent No.: US 10,053,397 B2
(45) Date of Patent: Aug. 21, 2018

(54) HYDRODEOXYGENATION OF OXYGENATES

(71) Applicant: PHILLIPS 66 COMPANY, Houston, TX (US)

(72) Inventors: Alexandru Platon, Bartlesville, OK (US); Edgar Lotero Alegria, Cleveland, OK (US)

(73) Assignee: Phillips 66 Company, Houston, TX (US)

( * ) Notice: Subject to any disclaimer, the term of this patent is extended or adjusted under 35 U.S.C. 154(b) by 80 days.

(21) Appl. No.: 15/439,989

(22) Filed: Feb. 23, 2017

(65) Prior Publication Data

US 2017/0240486 A1    Aug. 24, 2017

Related U.S. Application Data

(60) Provisional application No. 62/299,520, filed on Feb. 24, 2016.

(51) Int. Cl.
C07C 1/22 (2006.01)
C07C 7/10 (2006.01)
C07C 7/00 (2006.01)

(52) U.S. Cl.
CPC ............... *C07C 1/22* (2013.01); *C07C 7/005* (2013.01); *C07C 7/10* (2013.01); *Y02P 20/132* (2015.11)

(58) Field of Classification Search
CPC ............. C07C 1/22; C07C 7/10; C07C 7/005
USPC ........................ 585/240, 802, 833
See application file for complete search history.

(56) References Cited

U.S. PATENT DOCUMENTS

2012/0172588 A1 *   7/2012   Qiao ..................... C07C 27/04
                                                                536/124

* cited by examiner

*Primary Examiner* — Thuan D Dang
(74) *Attorney, Agent, or Firm* — Phillips 66 Company

(57) ABSTRACT

The present disclosure relates generally to processes and systems for the hydrodeoxygenation of an oxygenate feedstock that increases the conversion of oxygenates to hydrocarbons while avoiding detrimental effects resulting from increasing the severity of the hydrodeoxygenation reaction.

3 Claims, 1 Drawing Sheet

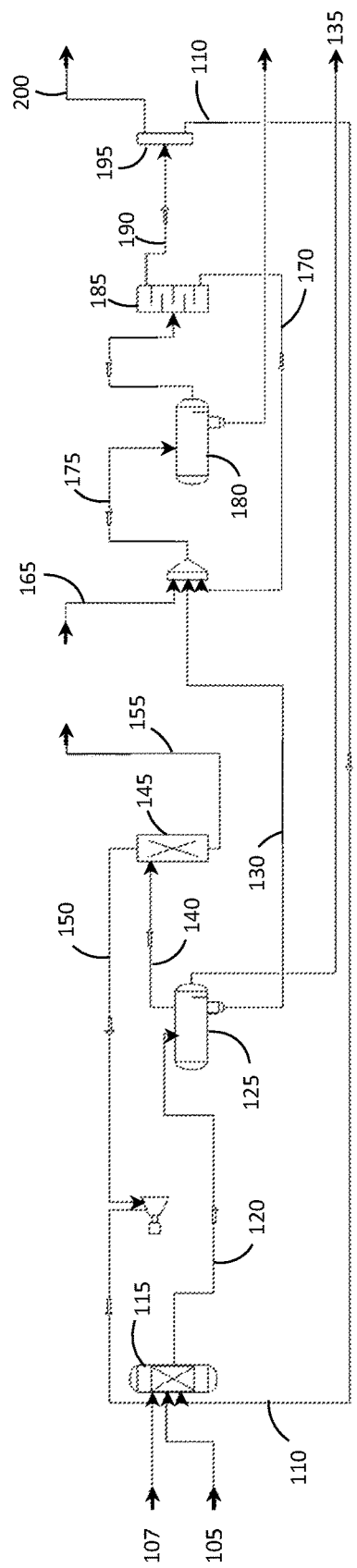

HYDRODEOXYGENATION OF OXYGENATES

CROSS-REFERENCE TO RELATED APPLICATIONS

This application is a non-provisional application which according to 35 U.S.C. § 119(e), claims the benefit of, and the right of priority to, U.S. Provisional Application Ser. No. 62/299,520 filed Feb. 24, 2016, entitled "Hydrodeoxygenation of Oxygenates," both of which are incorporated herein in their entirety, as permitted under 37 CFR 1.57(b).

STATEMENT REGARDING FEDERALLY SPONSORED RESEARCH OR DEVELOPMENT

None.

FIELD OF THE INVENTION

The present invention relates to improvements in the hydrodeoxygenation of oxygenates.

BACKGROUND

In typical applications for hydrocarbon production from oxygenated hydrocarbons, also known as oxygenates, the raw oxygenate feedstock is subjected to hydrodeoxygenation (HDO). Chemically, hydrodeoxygenation removes oxygen from the feedstock molecules in the presence of gaseous hydrogen and a HDO catalyst, and rejects it in the form of water. Oxygenates can have different relativities during HDO. Certain oxygenates, such as those with either low molecular weights or phenolic compounds, have a lower HDO reactivity than other oxygenates. Increasing the severity of the HDO process (e.g., increasing reaction temperature, increasing residence time, increasing hydrogen partial pressure) can be employed to insure these refractory oxygenates are converted. However, undesired side reactions such as cracking to lights and coking of the catalyst are also promoted at higher HDO severities. The final oxygenate conversion during HDO is typically a compromise between the product value lost in the form of unreacted oxygenates, and the cost savings in the form of higher overall HDO product yield and longer catalyst run times.

Following HDO, unreacted oxygenates in the initial HDO product will typically partition between the hydrocarbon and the aqueous portions of the initial HDO product stream. Because oxygenates are typically highly polar, the unreacted oxygenates tend to partition preferentially into the water phase of the initial HDO product. Although the hydrocarbon portion of the initial HDO product can be subjected to additional HDO polishing or separation, the aqueous portion containing large amounts of unreacted oxygenates typically is either discarded or subjected to an energy intensive separation of water from the oxygenates.

Subjecting the aqueous HDO product to additional HDO is extremely difficult due to the elevated water content which increases the heating and cooling requirements, damages the HDO catalyst, lowers the hydrogen partial pressure during subsequent HDO, and increases the required size and cost of the second HDO reactor.

Accordingly, a need exists for processes that allow more efficient HDO of oxygenates without increasing the severity of the process.

BRIEF SUMMARY OF THE DISCLOSURE

In certain embodiments of the present invention, there is provided a process comprising: A process for hydrodeoxygenation of oxygenates, comprising: a) contacting a feedstock comprising oxygenates with a hydrodeoxygenation catalyst in the presence of hydrogen gas at a temperature and pressure suitable for hydrodeoxygenation of at least a portion of the oxygenates to produce a partially-deoxygenated product; b) phase-separating the partially-deoxygenated product into an aqueous phase comprising unreacted oxygenates, a non-aqueous phase comprising hydrocarbons, and light gases comprising hydrogen; c) mixing the aqueous phase with a solvent that is water-immiscible and extracting unreacted oxygenates from the aqueous phase into the water-immiscible solvent, followed by separating the phases to produce a solvent comprising unreacted oxygenates; d) distilling the solvent comprising unreacted oxygenates to produce a separated solvent and separated unreacted oxygenates, where the separated unreacted oxygenates are utilized as at least a portion of the oxygenate feedstock.

In certain embodiments, the light gases are separated to recover hydrogen that is recycled for use in the HDO reaction.

In certain embodiments, the separated solvent is utilized as at least a portion of the water insoluble solvent.

BRIEF DESCRIPTION OF THE DRAWINGS

A more complete understanding of the present invention and benefits thereof may be acquired by referring to the follow description taken in conjunction with the accompanying drawings in which:

The FIGURE is a simplified schematic in accordance with an embodiment of the present disclosure.

The invention is susceptible to various modifications and alternative forms, specific embodiments thereof are shown by way of example in the drawings. The drawings may not be to scale. It should be understood that the drawings and their accompanying detailed descriptions are not intended to limit the scope of the invention to the particular embodiment disclosed, but rather, the intention is to cover all modifications, equivalents and alternatives falling within the spirit and scope of the present invention as defined by the appended claims.

DETAILED DESCRIPTION

The inventive process comprises a hydrodeoxygenation (HDO) process improvement that increases oxygenate conversion to liquid hydrocarbon fuels (or a component thereof) without the need to increase HDO severity, which would sacrifice the overall yield via: 1) increased production of light hydrocarbons from cracking, and 2) decreased catalyst lifespan due to an increased coking rate.

An embodiment of the inventive process and system 100 is generally illustrated in the Figure. The HDO reaction is conducted in HDO reactor 115 that contains an HDO catalyst (not depicted) and contains inlets for receiving an input of oxygenate feedstock 105, hydrogen gas 107, and recycled oxygenates 110. Following the HDO reaction in the HDO reactor 115, a first HDO product 120 is directed to a first separator 125 that is configured to phase-separate the first HDO product 120 into an aqueous phase 130 comprising unreacted oxygenates, a non-aqueous phase 135 comprising hydrocarbons, and light gases 140 comprising hydrogen. The light gases 140 are directed to a light gas fractionator 145 that produces a hydrogen fraction 150 that is recycled to the HDO reactor 115, while other light gases 155 are directed for use in other processes or combusted (not depicted).

The aqueous phase 130 is directed to a mixer 160 that also receives a fresh water-insoluble solvent 165 capable of dissolving unreacted oxygenates. The mixer 160 also receives recycled water-insoluble solvent 170. The mixer 160 is configured to combine the aqueous phase 130 with the water-insoluble solvent 170 and output the resulting emulsion 175 to a second separator 180 that is configured to allow simultaneous phase-separation of the aqueous phase 130 from the water-insoluble solvent 170 while simultaneously facilitating extraction of unreacted oxygenates from the aqueous phase into the water-insoluble solvent. A non-exclusive example of such a water-insoluble solvent is a hydrocarbon fraction rich in aromatics (e.g, FCC light cycle oil or FCC heavy cycle oil).

Further referring to the Figure, water-insoluble solvent containing extracted, unreacted oxygenates are directed from the second separator 180 to distillation column 185 to produce separated unreacted oxygenates 190 and water-insoluble solvent 170, which is returned to mixer 160. The separated unreacted oxygenates 190 are optionally directed trough a purge splitter 195 that either directs the unreacted oxygenates to be purged 200, or returned to HDO reactor 115 as recycled oxygenates 110.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. Thus, the invention disclosed herein is specifically intended to be as broad as the claims below and those variations and equivalents that are encompassed by the scope of the claims.

We claim:

1. A process for hydrodeoxygenation of oxygenates, comprising:
    a) contacting a feedstock comprising oxygenates with a hydrodeoxygenation catalyst in the presence of hydrogen gas at a temperature and pressure suitable for hydrodeoxygenation of at least a portion of the oxygenates to produce a partially-deoxygenated product;
    b) phase-separating the partially-deoxygenated product into an aqueous phase comprising unreacted oxygenates, a non-aqueous phase comprising hydrocarbons, and light gases comprising hydrogen;
    c) mixing the aqueous phase with a solvent that is water-immiscible, and extracting unreacted oxygenates from the aqueous phase into the solvent, followed by separating the phases to produce a solvent comprising unreacted oxygenates;
    d) distilling the solvent comprising unreacted oxygenates to produce a separated solvent and separated unreacted oxygenates, wherein the separated unreacted oxygenates are utilized as at least a portion of the feedstock of part a).

2. The process of claim 1, wherein the light gases are separated to recover hydrogen that is recycled for use in part a).

3. The process of claim 1, wherein the separated solvent is utilized as at least a portion of the water insoluble solvent of part c).

* * * * *